(12) United States Patent
Vogler et al.

(10) Patent No.: US 8,915,905 B2
(45) Date of Patent: Dec. 23, 2014

(54) APPARATUS FOR OPHTHALMIC LASER SURGERY

(75) Inventors: Klaus Vogler, Eckental/Eschenau (DE); Claudia Gorschboth, Nuremberg (DE)

(73) Assignee: WaveLight GmbH, Erlangen (DE)

( * ) Notice: Subject to any disclaimer, the term of this patent is extended or adjusted under 35 U.S.C. 154(b) by 1085 days.

(21) Appl. No.: 12/483,487

(22) Filed: Jun. 12, 2009

(65) Prior Publication Data

US 2010/0318073 A1 Dec. 16, 2010

(51) Int. Cl.
*A61F 9/008* (2006.01)
*A61F 9/01* (2006.01)
*A61B 18/20* (2006.01)

(52) U.S. Cl.
CPC ....... *A61F 9/008* (2013.01); *A61F 2009/00897* (2013.01); *A61F 9/0084* (2013.01); *A61F 2009/00872* (2013.01); *A61F 9/00827* (2013.01)
USPC ............................................................ 606/4

(58) Field of Classification Search
USPC .............. 606/4–6, 10–12; 359/290, 291, 298, 359/315, 318
See application file for complete search history.

(56) References Cited

U.S. PATENT DOCUMENTS 5,786,926 A * 7/1998 Yamada ......................... 359/250
6,530,916 B1 * 3/2003 Shimmick ......................... 606/5

FOREIGN PATENT DOCUMENTS

| DE | 102005013949 A1 | 9/2006 |
| EP | 1837696 A1 | 9/2007 |
| JP | 2000171742 A | 6/2000 |
| WO | 03032803 A2 | 4/2003 |

OTHER PUBLICATIONS

Google translate version of EP 1837696 submitted for increased clarity. Accessed Nov. 27, 2012.*
Hiromasa Oku and Masatoshi Ishikawa, "A Variable-Focus Lens with 1kHz Bandwidth Applied to Axial-Scan of a Confocal Scanning Microscope," IEEE, 2003, pp. 309-310.
Mao Ye, et al., "Variable-Focus Liquid Crystal Lenses used in Imaging System as Focusing Elements," IEICE Trans. Electron., vol. E91-C, No. 10, Oct. 2008, pp. 1599-1603.
Patent Cooperation Treaty—European Patent Office, "Notification of Transmittal of the International Search Report and the Written Opinion of the International Searching Authority, or the Declaration," International Application No. PCT/EP2009/004253, Nov. 4, 2009, 17 pages.
Wolfgang Mönch, et al., "Variable Brennweite durch flüssige Mikrolinsen," Photonik, Apr. 2005, pp. 44-46.

* cited by examiner

*Primary Examiner* — Ryan Severson
*Assistant Examiner* — Rachel S Papeika
(74) *Attorney, Agent, or Firm* — Haynes and Boone, LLP

(57) ABSTRACT

An apparatus for ophthalmic laser surgery comprises a source (28) for a pulsed femtosecond laser beam, a telescope (32) expanding the laser beam, a scanner (36) downstream of the telescope, for deflecting the laser beam in a plane perpendicular to the beam path, and also an f-theta objective (44) downstream of the scanner, for focusing the laser beam. In accordance with the invention, an entrance lens (52) of the telescope (32) takes the form of a controllable lens of variable refractive power. The entrance lens (52) is preferentially constituted by an electrically controllable liquid lens or liquid-crystal lens.

18 Claims, 2 Drawing Sheets

APPARATUS FOR OPHTHALMIC LASER SURGERY

Figure 1:
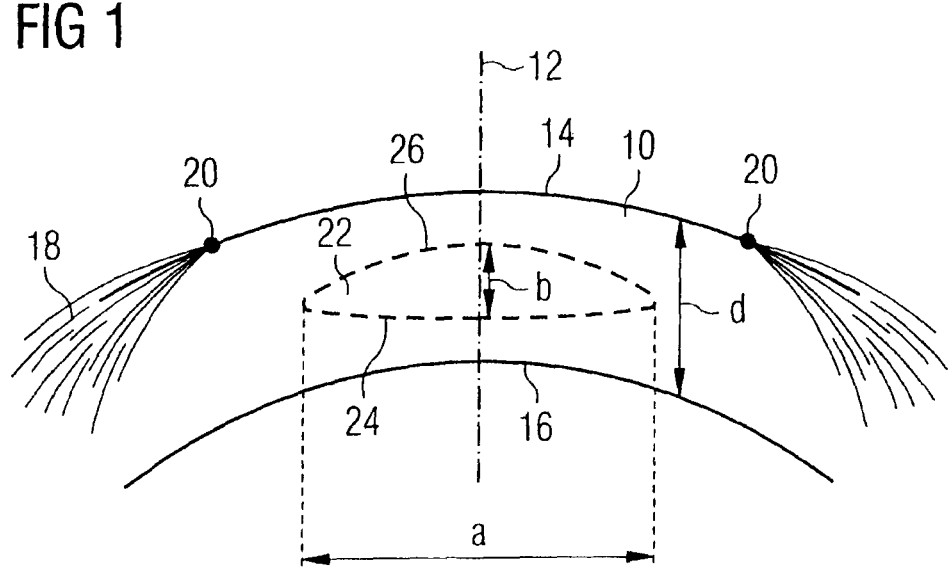

The invention relates to an apparatus for ophthalmic laser surgery. In particular, the invention relates to an apparatus for laser surgery that permits the focus of a laser beam provided by this apparatus to be displaced quickly in the z-direction, the expression 'z-direction' meaning, according to conventional notation, the direction of the beam path (direction of beam propagation). Any direction in a plane orthogonal to the z-direction is then to be understood as the x-y direction. In this plane the deflection of the laser beam by means of a scanner is then effected conventionally for the purpose of scanning a region of the eye to be treated by means of the laser beam.

Laser systems that emit short-pulse radiation within the femtosecond range are employed in ophthalmic surgery, inter alia, for the purpose of making intra-tissue incisions in the cornea but also in the human lens. The effect that is utilised in this connection is optical breakthrough, which results in a so-called photodisruption of the irradiated tissue. For the purpose of generating such photodisruptions, a comparatively strong focusing of the laser beam is required, which is achieved by a correspondingly high aperture of the focusing optics used for focusing. In known ophthalmic fs laser systems the focusing optics are usually constituted by a so-called f-theta objective which guarantees a plane-field imaging and avoids undesirable displacements of the beam focus in the z-direction in the course of scanning by the laser beam.

Fs laser systems have a firm place in ophthalmology, for example in LASIK applications, where LASIK stands for 'laser in-situ keratomileusis' and designates a corneal treatment technique for eliminating sight defects, in which firstly a small covering disc (the so-called flap), which is still partly connected to the corneal tissue, is cut out on the corneal surface, this flap is then folded aside, and subsequently the stromal tissue exposed after folding the flap away is ablated with shortwave laser light, for example with an excimer laser radiating at 193 nm, in accordance with an ablation profile ascertained for the individual patient. In this case the fs laser system is employed for the purpose of making the flap incision.

For the production of the flap incision, it is known to flatten the cornea of the eye to be treated by means of an impressed applanation plate and to guide the beam focus two-dimensionally in a plane within the cornea. On account of the plane-field imaging accomplished by the f-theta objective, in this case there is no need for a z-displacement of the beam focus. Only in the marginal region of the flap may a displacement of the focus locations in the z-direction be necessary if it is desired to guide the marginal incision of the flap upwards out of the stroma of the cornea.

For the purpose of focus displacement in the z-direction, various solutions have been proposed in the state of the art. WO 03/032803 A2 provides for displacing the focusing objective as a whole in the direction of the z-axis—i.e. along the beam path. A modification of this would be to construct the focusing objective as a zoom objective. However, both methods have the disadvantage that the mechanical displacement or the zoom setting of the focusing objective has to be effected very precisely, since it is transformed into a 1:1 repositioning of the focus location. For a desired displacement of the focus by a few µm between consecutive pulses of the laser beam a correspondingly fast mechanical displacement of the focusing objective or of a zoom lens of the objective by the same distance is therefore required. Conventional mechanical drives are not suitable for this.

An alternative solution is shown in DE 10 2005 013 949 A1. The laser system therein exhibits a two-lens beam expander taking the form of a telescope, a downstream scanner as well as, directly following the scanner, a focusing lens. The input lens, which is constructed as a converging lens, of the beam expander is displaceable in the beam direction, i.e. in the z-direction, by means of a linear drive. Such a displacement of the input lens changes the divergence of the laser beam emerging from the beam expander. Given a constant position of the focusing lens, in this way the focus location is shifted in the z-direction. One advantage of this solution, in comparison with a z-displacement of the focusing optics, lies in the better reproducibility and higher accuracy of displacement, because the optical imaging system transforms the displacement path of the input lens of the beam expander down to a displacement path of the focus location that is smaller by a factor of 10, for example. However, the achievable speed of repositioning of the input lens sets limits to the speed of displacement of the beam focus, which has been transformed into the focal plane. For a three-dimensional incision such as is required for a corneal lenticular extraction, the method of focus repositioning according to DE 10 2005 013 949 A1 is indeed distinctly faster than the method shown in WO 03/032803 A2, simply because in the case of the repositioning of the input lens of the beam expander the masses to be moved are substantially smaller than in the case of the repositioning of the entire focusing optics or even just of a single focusing lens. Current focusing optics may readily weigh several kilograms, which then have to be moved in vibration-free manner. The input lens of the beam expander, on the other hand, may possess a comparatively small aperture and may correspondingly be small and lightweight. Nevertheless, conventional linear drives do not satisfy the requirements if it is desired to carry out an intracorneal lenticular incision or another three-dimensional incision in acceptably short time with a sufficiently highly repeating laser. The speeds of repositioning that are possible for a reliable, non-tilting guidance of the input lens of the beam expander in the case of conventional linear drives amount to, for example, between about 1 mm/s and 3 mm/s and are possibly also feasible up to 5 mm/s with justifiable effort for the mechanical guidance of the input lens. For a lenticular incision, however, when use is being made of an fs laser repeating in the two-digit to three-digit kHz range or even still higher, with the same principle of the repositioning of the z-focus, speeds of repositioning of the input lens of at least 10 mm/s and above would be necessary, which cannot be attained with linear-drive systems currently available on the market, at least not with such systems that satisfy the requirements as regards the accuracy of adjustment.

The object of the invention is to create a laser apparatus that is better suited for three-dimensional incision guidance in ophthalmic surgery. For the purpose of achieving this object, in accordance with the invention an apparatus for ophthalmic laser surgery is provided, comprising: a source of a pulsed femtosecond laser beam; a telescope expanding the laser beam, having an input lens taking the form of a controllable lens of variable refractive power; a scanner downstream of the telescope, for deflecting the laser beam in a plane (x-y plane) perpendicular to the beam path; an at least single-lens focusing objective, in particular f-theta objective, downstream of the scanner, for focusing the laser beam; and a program-controlled electronic control arrangement which, for the purpose of achieving a predetermined incision profile that requires displacements of the beam focus (50) in the direction of the beam path (z-direction), is configured to bring about these displacements solely by control of the lens of variable refractive power, without changing the focusing setting of the focusing objective.

The lens of variable refractive power is preferentially electrically adjustable and may, for example, be a liquid lens operating in accordance with the principle of electrowetting (sometimes also designated as electrocapillarity), or alternatively a liquid-crystal lens. Liquid lenses are known as such and are based on the Lippmann effect; in this respect see, for example, the article by W. Mönch, W. F. Krogmann, H. Zappe: *Variable Brennweite durch flüssige Mikrolinsen* [Variable focal length by means of liquid microlenses], *Photonik* 4/2005, pages 44-46. As a result of applying an electrical voltage to an electrode arrangement of the liquid lens, the surface tension changes and, as a result, so does the curvature of a liquid interface. In turn, the alteration of the curvature brings about an alteration of the focal length of the liquid lens. In particular, liquid lenses enable an alteration of the refractive power of 10 dpt or more within a few milliseconds by variation of the applied electrical voltage.

Liquid-crystal lenses are likewise known as such and are based on the reorientation or/and local shifting of liquid crystals in a liquid-crystal layer formed from the liquid crystals and, for example, monomers in the presence of an electric field. The reorientation or shifting of the liquid crystals brings about an alteration of the refractive index of the liquid-crystal layer and, by virtue of this, an alteration of the refractive power of the lens.

The electric controllability of the lens of variable refractive power enables a distinctly faster focal displacement in the z-direction than a linear repositioning of the entire lens, and makes do without a mechanical repositioning device. As a result, high speeds of repositioning are made possible, in which connection on account of the avoidance of mechanical drive means and mechanically moved parts no friction forces arise (apart from internal friction of the liquid or of the liquid crystals). This ensures high reliability, a long service life and a high degree of robustness (no mechanical wear).

The fast focus displacement in the z-direction that is made possible by the invention makes it particularly attractive for use in ophthalmic applications that operate with highly repeating focused fs laser radiation and that for short treatment-times strive for a fast three-dimensional incision guidance. One possible application that can profit from this fast three-dimensional incision guidance is corneal lenticular extraction, in which for the purpose of refractive correction of the cornea an approximately lenticular volume element is cut out of the stroma of the cornea. A precise and fast three-dimensional positioning of the foci of the fs laser pulses is important for this. In the x-y direction this is no problem, by virtue of a correspondingly fast operation of the scanner. For example, conventional mirror scanners, which operate in accordance with the galvanometer principle, are readily able to guarantee the requisite deflections even at pulse-repetition rates within the MHz range. In the z-direction, through the use of a variable-refractive-power input lens of the telescope a travel of the beam focus in the high two-digit µm range up to the three-digit µm range is readily possible within a few milliseconds or at least a few tens of milliseconds. For a corneal lenticular extraction, for example, this allows the complete lenticular incision to be carried out in a few minutes (e.g. 2 to 4 minutes), limiting the inconvenience that the patient experiences in the course of such an operation to agreeably short lengths of time. In addition, the invention opens up the way towards refractive corrections of the eye without the hitherto customary use of an excimer laser, because the high precision and reproducibility of the z-positioning of the beam focus enables an incision guidance in the course of the lenticular extraction that is exactly matched to the sight defect to be eliminated.

EP 1 837 696 A1 already describes an optical imaging system with at least one focusing lens, with at least two lenses in a telescope and with a scanning unit, arranged in the beam path downstream of the telescope and upstream of the focusing lens, for the purpose of beam deflection in an x-y plane, wherein at least one of the telescope lenses is an electrically adjustable liquid lens, and wherein the liquid lens compensates the field curvature of the focusing lens. In the case of the invention, on the other hand, the variable-refractive-power lens has the task of realising the z-displacements of the beam focus that are predetermined by a given incision profile which is to be produced in the eye.

The variable-refractive-power lens in the case of the invention may be a converging lens; alternatively it may be a diverging lens.

The variable-refractive-power lens and actuating means assigned to it (including a voltage driver) have preferably been set up to bring about a displacement of the beam focus in the direction of the beam path by 100 µm in less than 30 ms, better in less than 24 ms, better still in less than 18 ms.

According to a further aspect of the invention, a process for laser-surgery eye treatment is provided that comprises the following steps:

providing a pulsed femtosecond laser beam directed onto an eye of a patient, scanning of the laser beam by means of a scanner in accordance with an incision profile to be realised in the eye that requires displacements of the beam focus (50) in the direction of the beam path, controlling an electrically controllable lens of variable refractive power for the purpose of achieving the displacements of the beam focus without changing the focusing setting of focusing means focusing the laser beam. The incision profile may, for example, represent a corneal lenticular incision.

Figure 2:
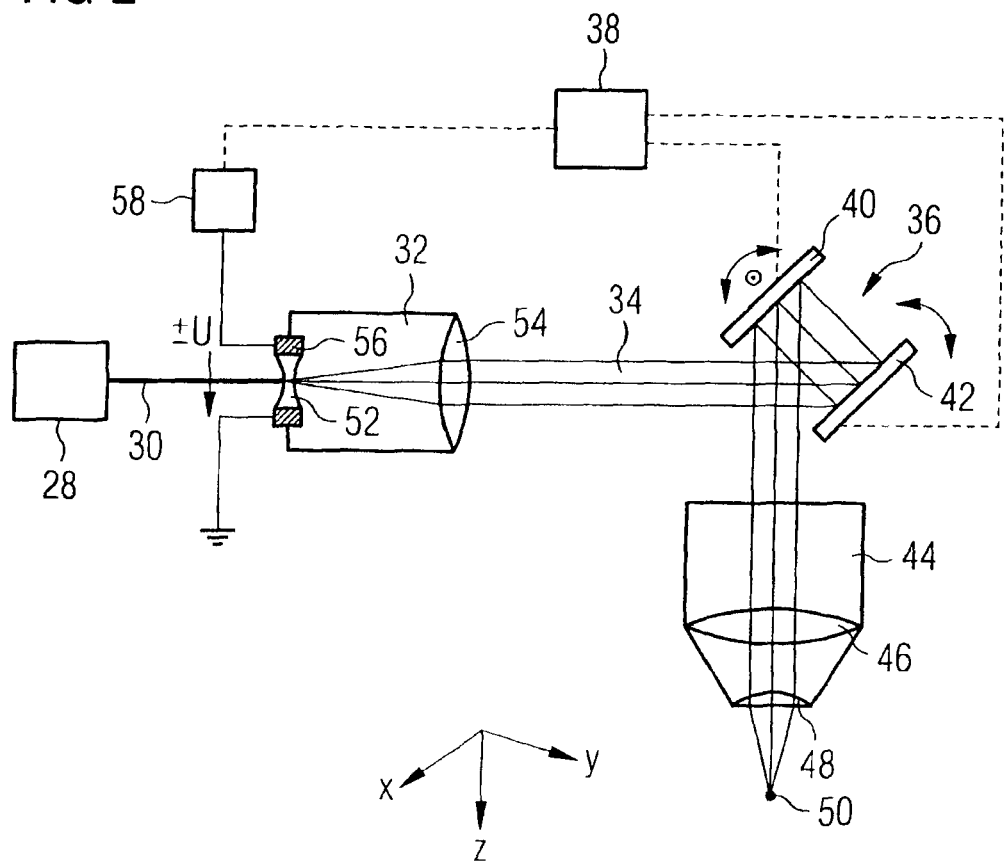

The invention will be elucidated further in the following on the basis of the appended drawings. Represented are:

FIG. 1 schematically in section, a part of the human eye including the cornea, with a corneal lenticular incision indicated, and FIG. 2 schematically, an example of an apparatus according to the invention for ophthalmic laser surgery.

Reference will firstly be made to FIG. 1. Therein the cornea, denoted by 10, of a human eye is shown in a sectional representation. The optic axis (visual axis) of the eye has been drawn with a dash-dotted line and is denoted by 12. The cornea 10 exhibits an anterior surface 14 and also a posterior surface 16. Its thickness d lies, in the typical human eye, within the range around 500 µm, variations in the upward or downward direction being possible, of course, from person to person. The sclera and the limbus of the eye are indicated in FIG. 1 at 18; the limbal margin is denoted by 20.

Drawn with a dashed line in FIG. 1 is furthermore an intracorneal—more precisely, intrastromal—lenticle 22 to be cut out by treatment with focused fs laser radiation, which is subsequently surgically removed through an opening to be introduced into the cornea 10. This opening can likewise be produced by means of a laser incision. The femtosecond lenticular extraction permits a correction of sight defects such as, for example, myopia and myopic astigmatism. Ordinarily the lenticle 22 is produced by means of a substantially flat rear incision 24 and a curved frontal incision 26. It will be understood that a flat rear of the lenticle is by no means obligatory. In principle, the incision guidance can be freely chosen for the upper side and for the underside of the lenticle. The lenticle diameter—denoted in FIG. 1 by a—lies, for example, within the range between 4 mm and 10 mm, whereas the maximal lenticle thickness, denoted by b, amounts, for example, to 50-150 μm. For example, in the case of values a=6-8 mm and b=80-100 μm, sight defects of about −5 dpt to −6 dpt can be corrected. It will be understood that both the lenticle diameter and the lenticle thickness may vary, depending on the severity of the sight defect to be corrected. Frequently the lenticle thickness will amount to some tens of μm, which, in conjunction with an approximately flat lenticle underside (defined by the rear lenticular incision 24), means that in the course of a line scan of a laser beam beyond the lenticular apex (that is to say, the place where the lenticle 22 has the greatest thickness) the beam focus of the laser beam has to execute a travel in the direction of beam propagation corresponding to the lenticle thickness.

Reference will now additionally be made to FIG. 2. The laser apparatus shown therein includes a femtosecond laser source 28—constituted, for example, by a fibre laser—which generates pulsed laser radiation 30 with pulse durations within the femtosecond range and with a pulse-repetition rate which preferentially lies within the high two-digit kHz range up to the three-digit kHz range or even in the MHz range. The laser beam 30 which is generated is expanded by a multi-lens beam expander 32. The expanded laser beam 34 subsequently reaches a scanner 36 which has the task of deflecting the laser beam 34 in an x-y plane orthogonal to the direction of beam propagation (z-direction; cf. the coordinate system that is also drawn in FIG. 2), and, by this means, of sweeping with the laser beam the region of the eye to be treated. In the exemplary case that is shown, the scanner 36 operates in accordance with the galvanometer principle and is constituted by two tiltable deflecting mirrors 40, 42 which are controllable by a control unit 38. It will be understood that scanners operating in accordance with other principles (e.g. scanning by means of a suitably controllable crystal) are equally possible.

Situated downstream of the scanner 36 is an f-theta focusing objective 44 with lenses 46, 48 which focus the laser beam onto a focus location 50. The construction of the focusing objective 44 as an f-theta objective brings about a plane-field imaging in which, independently of the deflection angle of the laser beam, the focus location 50 always lies in a flat plane orthogonal to the z-direction. It will be understood that the two-lens construction of the focusing objective 44 shown in FIG. 2 is only exemplary. The objective 44 may have been constructed with any other number of lenses.

In the exemplary case that is shown, the beam expander 32 is constituted by a Galilean telescope with an input lens 52 of negative refractive power (concave lens) and with an exit lens 54 of positive refractive power (converging lens). Alternatively, a Keplerian design of the telescope with two convex lenses is also possible (pot shown). The entrance lens 52 is constructed as a lens of variable refractive power, the refractive power of which is capable of being changed by means of an applied electrical driver voltage ±U. The achievable refractive-power deviation of the lens 52 preferentially lies distinctly above 10 dpt. The alteration of the refractive power of the entrance lens 52 brings about an alteration of the divergence of the laser beam impinging on the exit lens 54, and hence a z-shift of the beam focus 50. The entrance lens 52 is constructed as a liquid lens or as a liquid-crystal lens and possesses an electrode arrangement 56 indicated only schematically in FIG. 2, to which the driver voltage is applied. Dashed lines illustrate control connections between the control unit 38 and the deflecting mirrors 40, 42 as well as a voltage driver 58 for the driver voltage ±U.

The control unit 38 controls the voltage driver 58, and hence the electrode voltage at the entrance lens 52, in accordance with the incision profile to be realised in the eye. A corresponding control program for the control unit 38 is saved in a memory which is not represented in any detail. In the case of liquid lenses, which are based on the principle of electrowetting, the refractive power of the lens depends on the square of the applied voltage. Control of the focal length of the entrance lens 52 can therefore be effected with comparatively small voltage deviations in the case where this lens is constructed as a liquid lens. For example, with a voltage deviation of about 10 V, given suitable dimensioning of the entrance lens 52 a refractive-index deviation of about 10 dpt can readily be obtained (depending on the aperture and configuration of the electrostrictive lens 52). In this connection, given appropriate design the reaction-times of the liquid lens may lie within the range from a few tens of ms down to a few ms.

The focus of the f-theta objective 44 can consequently be repositioned in times that are necessary for an effective fast lenticular incision with an fs laser system. For example, a complete line scan can readily be carried out with a z-travel of the beam focus of about 100 μm within a period between about 10 ms and 40 ms. With the use, according to the invention, of electrically controllable variable-refractive-power lenses in the beam expander 32, focus-travel frequencies are consequently obtained such as are needed for meaningful application in the course of the femtosecond lenticular extraction.

Liquid lenses currently available on the market, which operate in accordance with the principle of electrowetting, contain liquids that are highly transparent within the range from about 300 nm to 1300 nm. Accordingly, for the lenticular extraction (and also for other corneal incisions) use may be made both of the fundamental wavelength located within the low infrared region of a typical fs laser source, and of a harmonic located within the UV region, for example the third harmonic of this fundamental wavelength.

The UV wavelength is particularly suitable for refractive correction by means of femtosecond lenticular extraction, since the requisite accuracies of the beam focusing are most likely to be attained with a wavelength around about 340 nm, for example. For example, a focus diameter of no more than 1 μm is striven for. With an NIR wavelength such small focus diameters can be obtained only with difficulty.

The design of the entrance lens 52 of the beam expander 32 in the form of a variable-refractive-power lens has the further advantage that use can be made of a lens with a relatively small aperture, for example with a lens diameter between about 2 mm and 6 mm. As a result, the driver voltage can be kept small, and faster switching-frequencies can be obtained.

Thirdly, the influence of any wavefront errors of the entrance lens 52 on the achievable focus quality is sufficiently small. Liquid lenses currently available on the market exhibit, for example, only a wavefront quality of λ/4, which in the case of use as a zoom lens in the focusing objective 44 would be insufficient for achieving a diffraction-limited focus.

The lens of variable refractive power that is used within the scope of the invention should be transmitting at least in respect of fs laser pulses within the NIR wavelength region, preferentially at least between about 1000 nm and 1100 nm. Overall it is desirable to enable a z-displacement of the beam focus of at least 300 μm, preferentially at least 350 μm and still more preferably at least 400 μm, solely by control of the lens of variable refractive power, without an adjustment of the focusing optics being additionally required for this purpose. Such a maximal focus travel should preferentially be achievable with a dioptric deviation of the lens of variable refractive power of at least 7.5 dpt, better at least 8 dpt and better still at least 8.5 dpt. The optical imaging system that images the generated laser beam onto the beam focus (i.e. telescope or beam expander, focusing objective and any optical elements arranged in between) should guarantee a corresponding transmission ratio. The accuracy of adjustment of the lens of variable refractive power within the working-deviation range (which, for example, may amount to about 9 dpt or about 10 dpt) should preferentially amount to at least 3%, better at least 2% and, by way of example, approximately 1%. A design in which a voltage deviation of about 1 V of a control voltage applied to the lens of variable refractive power brings about approximately a dioptric deviation of about 1 dpt, and simultaneously a dioptric deviation of about 0.1 dpt brings about a z-displacement of about 3-4 μm, can be obtained at any time with components currently available on the market.

The invention claimed is:

1. Apparatus for ophthalmic laser surgery, comprising:
a source of a pulsed femtosecond laser beam having a beam path, the pulsed femtosecond laser beam having an ultraviolet (UV) wavelength;
a telescope expanding the laser beam, having an input lens taking the form of a controllable concave lens of variable refractive power and an exit lens taking the form of a convex lens of fixed refractive power, the controllable concave lens of variable refractive power being transparent within the range from about 300 nm to about 1300 nm;
a scanner downstream of the telescope, for deflecting the laser beam in a plane perpendicular to the beam path;
a focusing objective downstream of the scanner for focusing the laser beam, the focusing objective being an f-theta objective formed of two lenses and configured to bring about a plane-field image such that a beam focus of the laser beam lies in a plane orthogonal to the beam path independent of the deflection of the laser beam by the scanner; and
a program-controlled electronic control arrangement in communication with at least the controllable concave lens of variable refractive power, the program-controlled electronic control arrangement controlling application of a voltage to the controllable concave lens of variable refractive power such that, for the purpose of achieving a predetermined incision profile for a lenticular extraction that requires displacements of the beam focus in the direction of the beam path to produce a curved front incision and a rear incision, a focus of the controllable concave lens of variable refractive power is adjusted based on the applied voltage to bring about the displacements of the beam focus in the direction of the beam path solely by control of the voltage applied to the controllable concave lens of variable refractive power, without changing a focussing setting of the focussing objective.

2. Apparatus according to claim 1, wherein the telescope includes only two lenses, the input lens and the exit lens.

3. Apparatus according to claim 1, wherein the concave lens of variable refractive power is a diverging lens.

4. Apparatus according to claim 1, wherein the concave lens of variable refractive power is electronically adjustable.

5. Apparatus according to claim 1, wherein the concave lens of variable refractive power is a liquid lens operating in accordance with the principle of electrocapillarity.

6. Apparatus according to claim 1, wherein the concave lens of variable refractive power is a liquid-crystal lens.

7. Apparatus according to claim 1, further including an actuating means associated with the concave lens of variable refractive power, the actuating means configured to bring about a displacement of the beam focus in the direction of the beam path by 100 μm in less than 30 ms.

8. Apparatus according to claim 7, wherein the actuating means is configured to bring about a displacement of the beam focus in the direction of the beam path by 100 μm in less than 24 ms.

9. Apparatus according to claim 7, wherein the actuating means is configured to bring about a displacement of the beam focus in the direction of the beam path by 100 μm in less than 18 ms.

10. An apparatus for ophthalmic laser surgery, comprising:
a laser source producing a pulsed laser beam;
a telescope in optical communication with the laser source, the telescope including a convex input lens and a convex exit lens, wherein the convex input lens is a controllable lens of variable refractive power, wherein the refractive power of the controllable lens is dependent upon a voltage applied to the controllable lens, and wherein the convex exit lens is a fixed lens of fixed refractive power;
a scanner in optical communication with the telescope downstream of the telescope, the scanner controlling deflection of the laser beam in a plane perpendicular to a beam path of the laser beam;
a focusing objective in optical communication with the scanner downstream of the scanner, the focusing objective being an f-theta objective configured to bring about a plane-field image such that a beam focus of the laser beam lies in a plane orthogonal to the beam path, independent of the deflection of the laser beam by the scanner; and
a controller in communication with the laser source, the controllable lens of the telescope, and the scanner, the controller controlling application of the pulsed laser beam to portions of the eye in accordance with a predetermined lenticular incision profile that requires variation in the position of a focal point of the pulsed laser beam in a plane perpendicular to the beam path and along the axis of the beam path to produce front and rear lenticular incisions, wherein the controller controls the position of the pulsed laser beam in the plane perpendicular to the beam path using the scanner, wherein the controller controls the position of the pulsed laser beam along the beam path by adjusting a voltage applied to the controllable lens of variable refractive power such that a focus of the controllable lens of variable refractive power is adjusted based on the applied voltage to bring about the variations in the position of the focal point of the pulsed laser beam along the axis of the beam path only through adjustment of the voltage applied to the controllable lens of variable refractive power and with the focusing objective remaining in a fixed position.

11. The apparatus of claim 10, wherein the lens of variable refractive power is a converging lens.

12. The apparatus of claim 10, wherein the telescope includes only two lenses, the convex input lens and the convex exit lens.

13. The apparatus of claim 10, wherein the lens of variable refractive power is a liquid lens.

14. The apparatus of claim 13, wherein the liquid lens has a diameter between about 2 mm and about 6 mm.

15. The apparatus of claim 13, further comprising an actuator for applied the voltage to the controllable lens of variable refractive power.

16. The apparatus of claim 15, wherein the actuator is configured to bring about a displacement of the beam focus along the axis of the beam path by 100 μm within a period of about 10 ms and about 40 ms.

17. The apparatus of claim 16, wherein the actuator is a voltage driver.

18. The apparatus of claim 17, wherein the laser source has an infrared wavelength.

* * * * *